United States Patent [19]
Gebhard

[11] Patent Number: 6,001,070
[45] Date of Patent: Dec. 14, 1999

[54] FACIAL IRON

[76] Inventor: Albert Gebhard, 2101 E. Alameds Ave., Denver, Colo. 86209

[21] Appl. No.: 09/240,561

[22] Filed: Jan. 29, 1999

Related U.S. Application Data

[63] Continuation-in-part of application No. 09/150,325, Sep. 9, 1998, abandoned.

[51] Int. Cl.$^6$ ...................................................... A61B 17/00
[52] U.S. Cl. .......................... 601/15; 601/16; 606/240.35
[58] Field of Search ............................... 601/1, 2, 15–16, 601/18–21, 69–74, 118–135; 606/204.35

[56] References Cited

U.S. PATENT DOCUMENTS

| | | |
|---|---|---|
| 3,507,493 | 4/1970 | Robins . |
| 3,911,909 | 10/1975 | Di Matteo . |
| 4,189,141 | 2/1980 | Rooney . |
| 4,291,685 | 9/1981 | Taelman . |
| 4,787,373 | 11/1988 | Vogel . |
| 4,892,092 | 1/1990 | Klein . |
| 5,218,955 | 6/1993 | Gueret . |
| 5,458,561 | 10/1995 | Schweisfurth . |
| 5,501,646 | 3/1996 | Miller . |
| 5,551,949 | 9/1996 | Kim ............................................ 601/15 |
| 5,582,585 | 12/1996 | Nash-Morgan . |
| 5,709,705 | 1/1998 | Belcher . |
| 5,746,702 | 5/1998 | Gelfgat et al. . |

*Primary Examiner*—Glenn E. Richman
*Attorney, Agent, or Firm*—Patent Law Offices of Rick Martin, P.C.

[57] ABSTRACT

The present invention is a facial iron comprising a heating element and separate charging base. The facial iron heating element has a spoon shaped heating surface for applying heat to a users skin. The heating surface is attached to a handle having LED's for indicating the charge state of the heating element. The facial iron is constantly being recharged when it is in the charging base. A thermostatically controlled circuit activates the heating element when the temperature of the heating surface falls below a certain temperature. It activates the heating element when the temperature of the heating element reaches a preset temperature. The invention also comprises a three position switch allowing the invention to be shut off and stored in a charged condition for later use.

20 Claims, 4 Drawing Sheets

FACIAL IRON

REFERENCE TO RELATED APPLICATIONS

This application is a continuation-in-part of U.S. patent application Ser. No. 09/150,325 filed Sep. 9, 1998, abandoned.

FIELD OF THE INVENTION

The field of the present invention relates to cosmetic devices, more particularly to facial irons for alleviating or reducing wrinkles on the face of a user through the application of massage and heat.

BACKGROUND OF THE INVENTION

Cosmetic devices know in the art are used to apply cremes and ointments to a person's face. Heated surfaces are taught that, when applied to the skin, the heated surface causes the creme to be more readily absorbed by the skin. The iron used to apply the heat generally is heated by a remote element, and is then applied to a user's face. The iron heater is activated by plugging the iron into a wall socket. The device warms the iron, which is then applied to the face of a user.

Representative of the art is:

U.S. Pat. No. 5,746,702 (1998) to Gelfgat et al. discloses an improvement for devices which provide local massage of the facial skin for improvement of the effectiveness of the massage while making the device more ergonomic.

U.S. Pat. No. 5,709,705 (1998) to Belcher discloses the reduction of facial wrinkles by rolling the face and scalp with implements having free wheeling rollers.

U.S. Pat. No. 5,582,585 (1996) to Nash-Morgan discloses a disposable adhesively engagable neck and facial wrinkle gathering device.

U.S. Pat. No. 5,501,646 (1996) to Miller discloses a jaw and neck muscle exercise apparatus which includes a spring-loaded support arm attached to a soft chin support on one end and to a chest plate on the other end.

U.S. Pat. No. 5,458,561 (1995) to Schweisfurth discloses a massage device for the rolling massage of skin areas and reflex zones of the human body which includes a shaft mounted on a handle and massage rings or rolling bodies which are freely rotatably mounted on the shaft.

U.S. Pat. No. 5,218,955 (1993) to Gueret discloses a massage device which is adapted to be applied to the skin.

U.S. Pat. No. 4,892,092 (1990) to Klein discloses a facial mask for use in effecting isometric toning of facial muscles.

U.S. Pat. No. 4,787,373 (1988) to Vogel discloses a facial ironer. The facial ironer apparatus includes a housing which holds a heating element having a base and a head. There is an electrical cord connecting the apparatus to a conventional AC electrical cord outlet. There is a thermostatic switch in the housing for maintaining the temperature of the heating element at a predetermined setting. The facial ironer itself is demountably attached to the head of the heating element. The facial ironer includes a triangular-shaped soleplate. The soleplate is heated by the transfer of heat from the heating element.

U.S. Pat. No. 4,291,685 (1981) to Taelman discloses a therapeutic heat and cosmetic applicator. A cosmetologist cleans the skin with unscented makeup remover and lotions. Then a lubricant is applied with a small hot iron to soften the pores. This face ironing is followed by a herbal or seaweed steam facial, manual and deep-pore cleaning.

U.S. Pat. No. 4,189,141 (1980) to Rooney discloses a mask which completely covers the face and which has pockets in which weights may be placed while the facial muscles are exercised.

U.S. Pat. No. 3,911,909 (1975) to Di Matto discloses a facial wrinkle remover.

U.S. Pat. No. 3,507,493 (1970) to Robins discloses an eye and forehead area muscle exerciser in which a portion of the face is covered by the device to hold the facial muscles against movement.

What is needed is a portable facial iron for applying a heated facial message for an effective 15 to 30 minute period. What is needed is a facial iron having a spoon shaped heating element. What is needed is a facial iron having a temperature control circuit. What is needed is a facial iron having a separate charger base and rechargeable batteries for convenience and safety. What is needed is a facial iron having an ergonomically shaped handle for improved ease of control and leverage. What is needed is a facial iron having LED's for indicating the charge and operational status of the heating element. What is needed is a facial iron having a three position switch. The present invention meets all these needs.

SUMMARY OF THE INVENTION

The primary aspect of the present invention is to provide a facial iron for providing a controlled, heated massage to a users face.

Another aspect of the present invention is to provide a facial iron having rechargeable batteries.

Another aspect of the present invention is to provide a facial iron having a spoon shaped heating element.

Another aspect of the present invention is to provide a facial iron having LED's for indicating the charge status of the heating element.

Another aspect of the present invention is to provide a facial iron having an ergonomically shaped handle.

Another aspect of the present invention is to provide a facial iron having a temperature control circuit.

Another aspect of the present invention is to provide a facial iron having a separate charger base.

Another aspect of the present invention is to provide a facial iron having a three position switch.

Other aspects of this invention will appear from the following description and appended claims, reference being made to the accompanying drawings forming a part of this specification wherein like reference characters designate corresponding parts in the several views.

The invention comprises a facial iron having a charger base. The facial iron contains a battery pack. The battery pack charge status is indicated by a set of LED's. A red LED in the iron indicates the functional status of the unit. The red LED illuminates when the batteries are discharging and the spoon shaped heating surface is heating. When the facial iron is in the charger base, the red LED in the base is illuminated until the batteries in the facial iron are fully charged. When they are fully charged, a green LED in the base lights up. When the facial iron is removed from the charger base the LED's go out. The batteries then heat a heating element adjacent to the spoon shaped heating surface on the facial iron to approximately 110 degrees F. A red LED on the iron illuminates while the iron is in use and the batteries are discharging. The facial iron circuitry includes a thermistor and controller designed to maintain the spoon shaped surface at a temperature of 98° to 120° F. In the preferred embodiment the range is 108° to 110° F. A full charge allows for up to 30 minutes of use. When the charge in the facial iron is exhausted, it is returned to the charger base where the batteries are recharged. The facial iron decreases wrinkles in a user's face through heated massage. A three position switch allows a user to operate the invention in the preferred mode; to turn on the invention regardless of its location; or, to turn off the invention upon removal from the charger for use at a later time.

Alternate embodiments include an iron having a 120V electrical cord for connecting the facial iron directly to an outlet for use. The iron maintains heat on the spoon shaped surface while it is plugged into the outlet. Yet another alternate embodiment includes an iron having rechargeable batteries which are recharged by connecting the iron to a recharger which plugs into an outlet, such as the type in use with portable rechargeable shavers. The iron is then disconnected from the cord for use.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF THE PREFERRED EMBODIMENT

Figure 1:
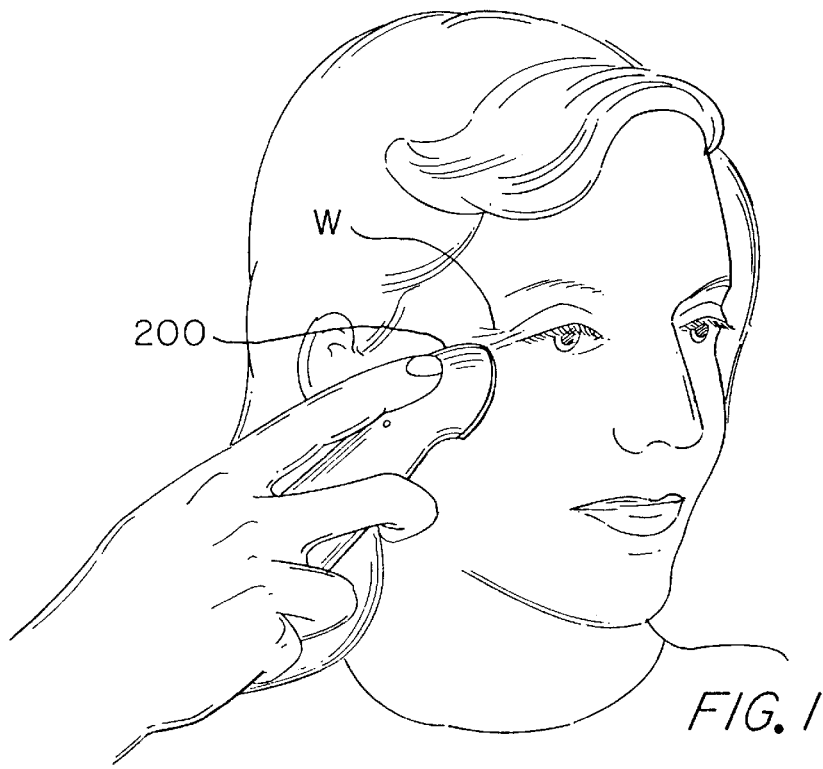
FIG. 1 is a top perspective view of a user massaging her face with the iron portion of the preferred embodiment.

FIG. 1 is a top perspective view of a user massaging her face with the preferred embodiment. Iron 200 is shown in use by a user. Iron 200 is applied to areas of a user's face where wrinkles W are located, such as around a user's eyes. Use in other locations of a user's face is possible due to the specialized shape of the spoon shaped heating surface.

Figure 2:
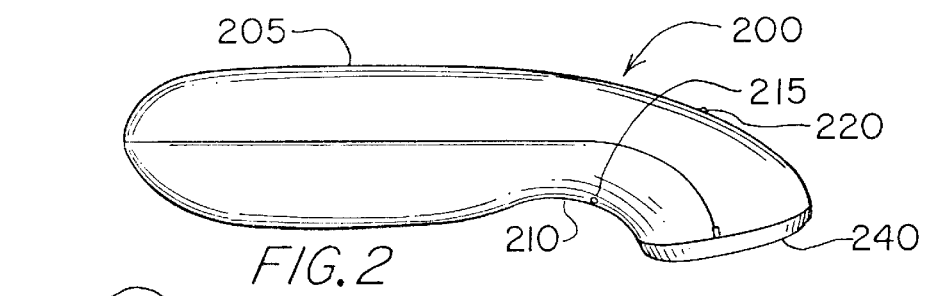
FIG. 2 is a side elevation view of the iron.

FIG. 2 is a side elevation view of the iron. Spoon shaped heating surface 240 is attached to the handle 205. Recess 210 in handle 205 allows for ease of holding. Handle 205 is ergonomically shaped allowing a user to more effectively control the manipulation of the spoon shaped heating surface. For example, placement of a user's palm upon the back of handle 205 results in greater leverage for applying pressure to a user's facial features, in particular, wrinkles. Electrical contact 215 provides the connection between the charger base (shown in FIG. 4) and the rechargeable batteries contained within the handle 205.

Figure 3:
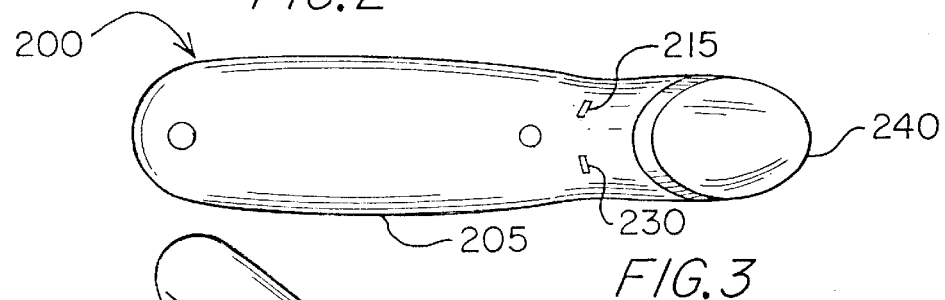
FIG. 3 is a bottom plan view of the iron.

FIG. 3 is a bottom plan view of the iron. Spoon shaped heating surface 240 it attached at one end of handle 205.

Figure 8:
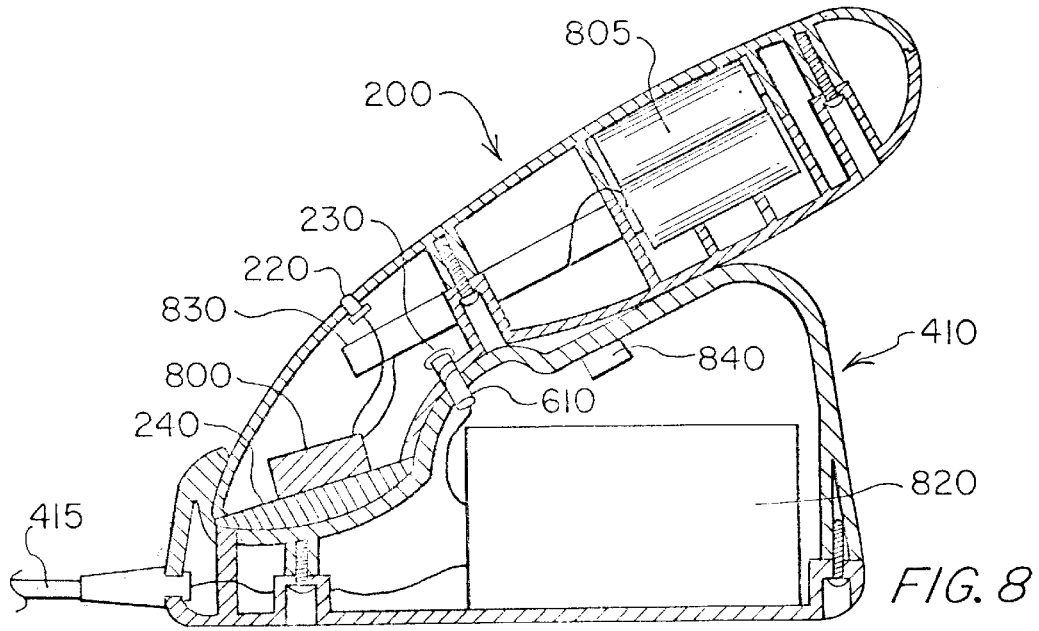
FIG. 8 is a longitudinal sectional view of the preferred embodiment.
Figure 9:
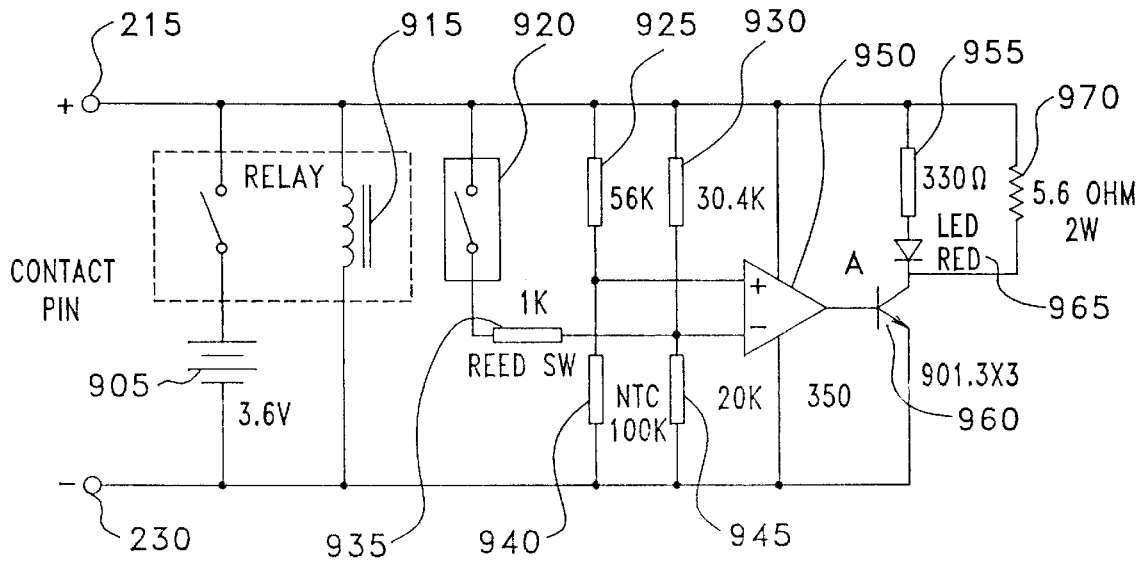
FIG. 9 is an electrical schematic drawing of the iron for the invention.

Spoon shaped heating surface 240 may comprise any heat conductive material, including metal and plastic, known in the art. It may also comprise metal impregnated plastic, also known in the art. Spoon shaped heating surface 240 generally describes any solid section of an elliptically shaped solid, the convex surface of the solid comprising the spoon shaped heating surface. The section may also be oval or spherical. In the preferred embodiment, the spoon shaped surface comprises a narrower end and a wider end, in a form which may be described in part as "egg-shaped", each being convex, thereby allowing application of the surface to a wide variety of a user's facial features. For ease of reference, and not by way of limitation, reference to the described surface shall be to the "spoon shaped heating surface". Electrical contacts 215 and 230 provide the connection between the charger (not shown) and the rechargeable batteries in the handle 205 as shown in FIG. 8. If the red LED 220 on FIG. 2, on the iron is illuminated, this indicates the batteries are discharging to heat the spoon shaped heating surface. It takes approximately 40 seconds for the spoon shaped heating surface 240 to reach the operating temperature of 98° F. to 120° F. The preferred embodiment operates in the range of 108° F. to 112° F. The electronic circiut described in FIG. 9 controls the temperature of the spoon shaped heating surface to approximately plus or minus 2° F. The current to the heater element is 650 mA to 750 mA. Three AA batteries, ¾ size—known in the art, should maintain this heat for up to 30 minutes. The heat in the spoon shaped surface is thermostatically controlled by a thermostat as shown in FIG. 9. Once use of the iron is completed, the iron is returned to the charger for recharging of the batteries to full charge.

Figure 4:
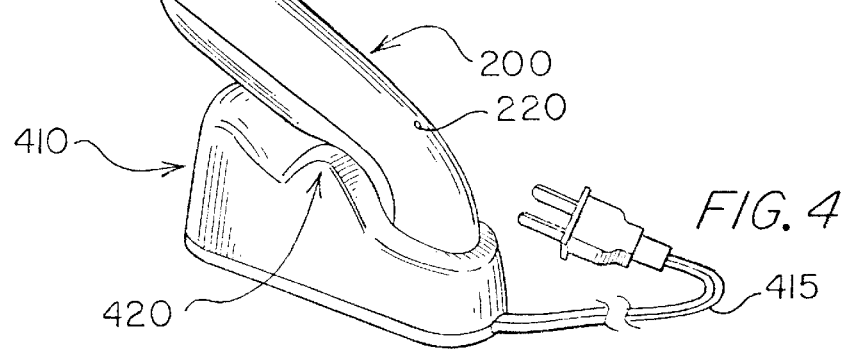
FIG. 4 is a perspective view of the preferred embodiment.

FIG. 4 is a perspective view of the preferred embodiment. Iron 200 is received by charger 410. Electrical cord 415 is used to connect charger 410 to any standard 120V AC supply. Electrical cord 415 may comprise any plug type necessary to accommodate the electrical system in the country of use, for example, 220V in Europe. Contour 420 allows the iron 200, having a co-operating contoured shape, to be received by charger 410. The charger 410 is plugged into a standard 120V outlet. When the iron is placed in the charger, the quick charge of the iron rechargeable batteries occurs. The rechargeable batteries typically consist of 3 AA batteries. The red LED in the charger base, see FIG. 6, illuminates as the batteries in the iron are being recharged. The current from the charger base to the iron batteries is 80 to 120 mA. After 3–5 hours the batteries are completely charged. Once the charging is complete the red LED turns off and the green LED illuminates. The charger 410 is then delivering 0 mA to the iron batteries. If the iron 200 is removed and used and returned to the charger, the charger will reactivate at 80 mA. The red LED will illuminate for as long as charging takes. The green LED will then illuminate again once the batteries are recharged, indicating the iron ready for use.

Figure 5:
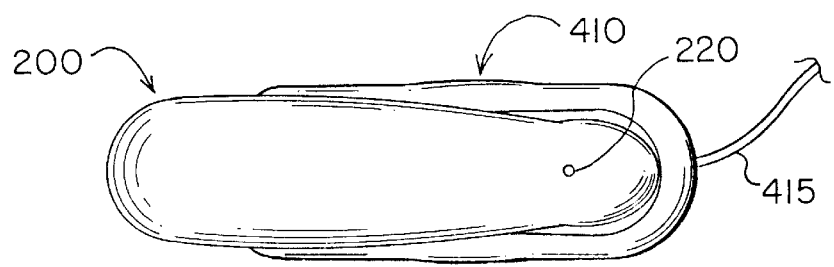
FIG. 5 is a top plan view of the preferred embodiment.

FIG. 5 is a top plan view of the preferred embodiment. Iron 200 is received by charger 410. AC power cord 415 allows connection to a 120V wall socket. Red LED 220 illuminates to indicate the spoon shaped heating surface is heating.

Figure 6:
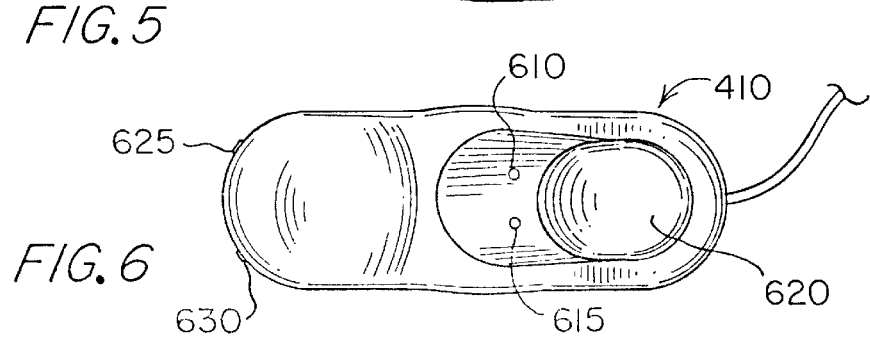
FIG. 6 is a top plan view of the charger.

FIG. 6 is a top plan view of the charger. Charger 410 has two electrical contacts 610 and 615 which electrically connect to contacts 215 and 230 in FIG. 3 to allow charging of the rechargeable batteries. Recess 620 receives the spoon shaped heating surface when the iron (not shown) is placed in the charger 410. Operation of green LED 625 and red LED 630 are described in FIG. 4.

Figure 7:
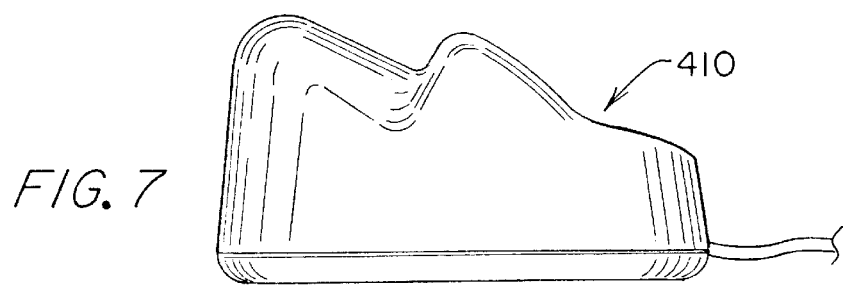
FIG. 7 is a side elevation view of the charger.

FIG. 7 is a side elevation view of the charger 410 without the iron.

FIG. 8 is a side elevation cut-away view of the preferred embodiment. Contained within iron 200 are rechargeable batteries 805. Red LED 220 illuminates when the heating element 800, which is connected to the spoon shaped heating surface 240, is operating. Electrical contact 230 on the iron 200 contacts electrical contact 610 on the charger 410. This allows the batteries 805 to be recharged while the iron is in the charger. The circuitry for charging the iron and controlling the operation of the iron are set forth in FIGS. 9 and 10. Charger electronics 820, known in the art, are contained within charger 410. Iron electronics 830 as described in FIG. 9 are contained within iron 200.

FIG. 9 is an electrical schematic drawing of the iron for the invention. Contacts 215 and 230 are described in FIG. 3. Rechargeable batteries 905 are in series with switch 910. Relay 915 causes relay contacts to close when the iron is placed in the charger. Magnetic reed switch 920 turns on the heater when the iron is removed from the charger. Magnetic reed switch 920 cooperates with magnet 840 on FIG. 8, contained within the charger. Resistor 935 protects op amp 950. Switch 920 closes the circuit to op amp 950. Resistors 925, 930, 940 and 945 determine the voltage delivered to the inverting and non-inverting inputs of op amp 950. Output from op amp 950 determines the state of transistor 960. The heater circuit comprises resistor 955, thermistor 970 and red LED 965. When the iron is being recharged in the charger, transistor 960 opens the heater circuit. When the iron is removed from the charger, relay 915 closes switch 910 thereby providing a voltage of 3.6 V across the circuit. This causes op amp 950 to output a voltage to transistor 960, which changes state and closes the heater circuit. Once the heater circuit is closed, current flows through thermistor 970 and red LED 965 thereby heating the spoon shaped heating surface. Red LED 965 illuminates when thermistor 970 is operating. Once the voltage delivered to the circuit by the batteries reaches a predetermined level, transistor 960 changes state and opens the heating circuit.

Figure 10:
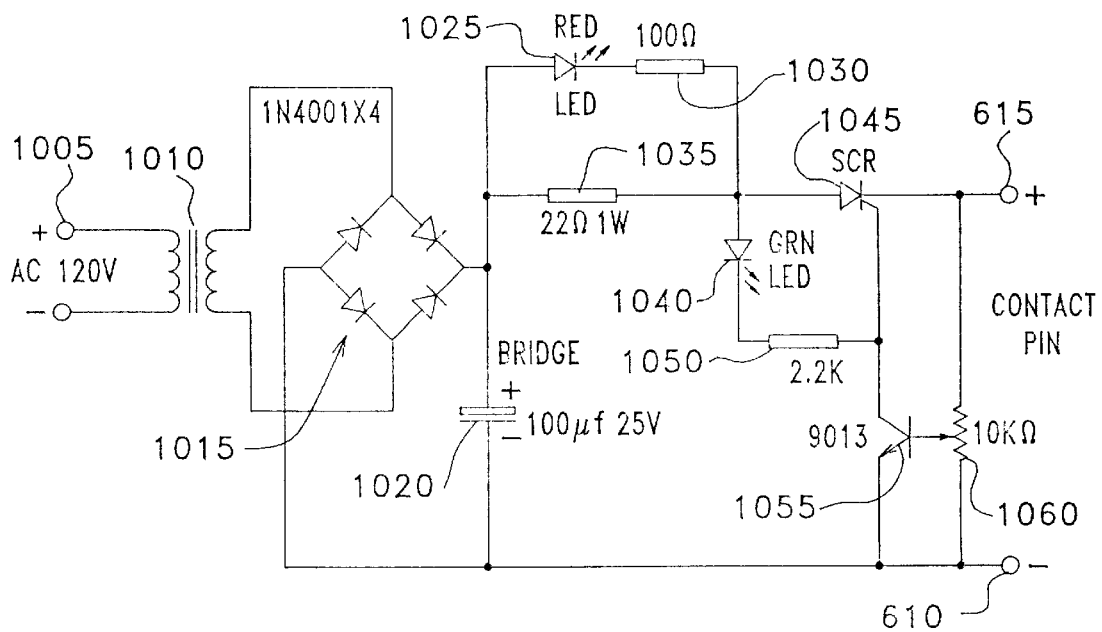
FIG. 10 is an electrical schematic drawing of the charger for the invention.

FIG. 10 is an electrical schematic drawing of the charger for the invention. AC power cord 1005 is connected to rectifier bridge 1015 through transformer 1010. Rectifier bridge 1015 rectifies the AC signal to a DC signal. Capacitor 1020 smoothes the rectified output waveform from rectifier bridge 1015. Red LED 1025 is in series with resistor 1030. Green LED 1040 is in series with resistor 1050. Resistor 1035 is in parallel with red LED 1025 and resistor 1030. While the charger is recharging the iron, red LED 1025 is illuminated. Current flows through SCR 1045 to contact 615 when the iron is in the charger. As charging is completed, the voltage across contacts 615 and 610 decreases until SCR 1045 changes state. Variable resistor 1060 determines the resistance between contacts 615 and 610. Transistor 1055 controls the value of variable resistor 1060. This in turn short circuits the charging current which eliminates the charging current through the iron. Once charging is complete the red LED 1025 goes out and green LED 1040 is illuminated.

Figure 11:
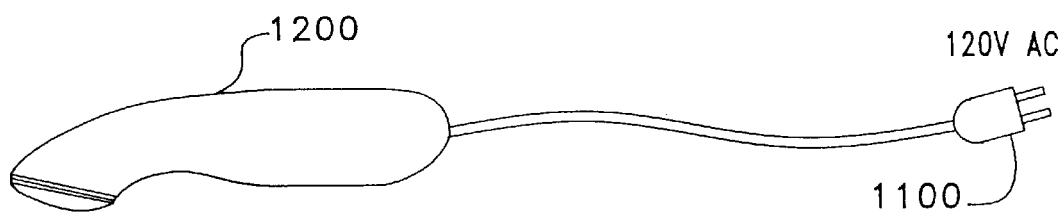
FIG. 11 is a side view of an alternate embodiment.

FIG. 11 is a side view of an alternate embodiment. In this alternate embodiment, an electric cord 1100 is used to plug the iron 1200 directly into a 120V outlet. The iron is used while it is plugged into the outlet. The heating element is connected in series with a thermostat. The heating element is heated to and maintained at 108° to 120° F.

Figure 12:
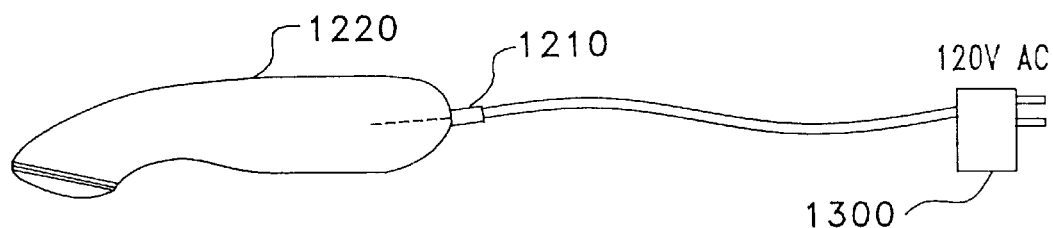
FIG. 12 is a side view of an alternate embodiment.

FIG. 12 is a side view of an alternate embodiment. Recharger 1300 is plugged into a 120V outlet. It is connected to iron 1220 by a plug 1210. Plug 1210 is disconnected once the rechargeable batteries are charged. The rechargeable batteries are 6V and are known in the art. The iron circuit is as shown in FIG. 9. In yet another alternate embodiment, the wall unit 1300 comprises a transformer and rectifier circuit which provides a low voltage output to the iron 1220. A thermostat contained within the iron maintains the temperature of the heating surface at 108 to 120° F.

Figure 13:
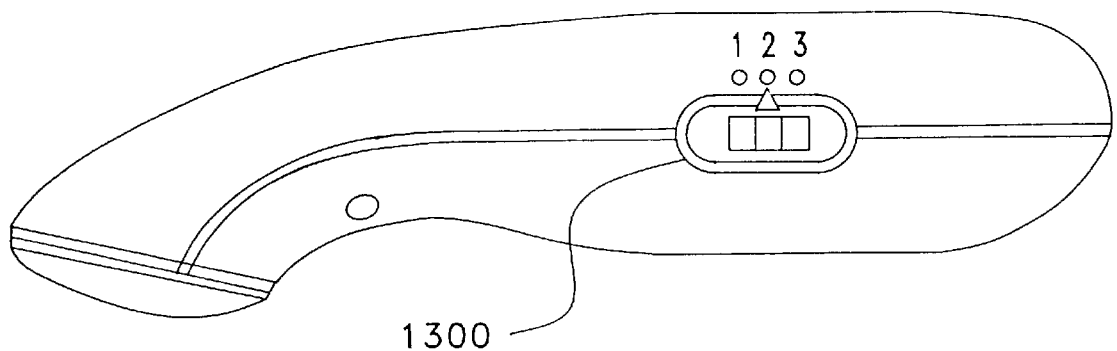
FIG. 13 is a schematic depicting a three position switch.

FIG. 13 is a schematic depicting an alternate embodiment showing a three position switch. Three-position switch 1300, known in the art, is connected into the circuit in FIG. 9 to operate in co-operation with magnetic reed switch 920 and relay 915.

Switch 1300 may be placed in one of three positions. In position 1, the invention is placed in the charger 410 for battery recharging. In position 1, thermistor 970 is activated upon removal from the charger, as described above in FIG. 9.

In position 2, thermistor 970 is activated regardless of the status or location of the invention. This is a result of switch 1300 closing a circuit around relay 915 and magnetic reed switch 920, thereby directly activating thermistor 970. In this position 2, a user de-activates the invention by returning the switch 1300 to position 1, for return to the charger, or position 3 as described below.

In position 3, the thermistor or heating element circuit is "opened" so that it is not possible for the thermistor to be activated. This is accomplished by switch 1300 opening the circuit connection to ground, thereby preventing activation of the thermistor 970. This allows a user to store the invention, without it being in the charger, with fully charged batteries for use at a later time, for example, at a location where the charger is not available. To use at a later time, a user simply moves switch 1300 from position 3 to position 2. Once the user has completed use of the invention, the user places the switch in position 3 to de-activate the thermistor circuit; or to position 1 with the return of the facial iron to the charger base for re-charging the batteries as described above.

Although the present invention has been described with reference to preferred embodiments, numerous modifications and variations can be made and still the result will come within the scope of the invention. No limitation with respect to the specific embodiments disclosed herein is intended or should be inferred.

I claim:
1. A facial iron comprising:
    a hand-held iron having a spoon shaped surface;
    a power source and a heater within said iron for heating said spoon shaped surface;
    a control circuit for controlling a preset temperature of said spoon shaped surface; and
    a charger remote from said power source for charging said power source.
2. The facial iron as in claim 1, wherein said power source comprises rechargeable batteries.
3. The facial iron as in claim 1, wherein said charger comprises a base for removably holding said iron.
4. The facial iron as in claim 1, wherein said control circuit comprises:
    a plurality of lights for indicating a charge status of the power source;
    a thermistor for maintaining a temperature of the spoon shaped surface; and
    means for activating said power source when said power source is removed from said base.
5. The facial iron as in claim 4, wherein the temperature of the spoon shaped surface is in a range of 98 to 120 degrees F.

6. The facial iron as in claim 5, wherein said iron weighs in a range of 3 to 6 ounces.

7. The facial iron as in claim 5, wherein said power source maintains said temperature range for over fifteen minutes.

8. The facial iron as in claim 1, wherein said spoon shaped surface comprises a heat conductive material located at a distal end of said iron.

9. A method of reducing facial wrinkles comprising the steps of:

connecting a surface to a power source and a heater;

containing said surface and said power source and heater in a hand-held iron;

charging said power source within said hand-held iron with a charger;

removing said iron from said charger;

heating said surface with said power source and heater to a predetermined temperature;

maintaining said surface at a predetermined temperature with a control circuit;

applying said surface to a user's face to treat wrinkles; and returning said hand-held iron to said charger to recharge said power source.

10. The method of reducing facial wrinkles as in claim 9, wherein the predetermined temperature comprises a range of 108 to 120 degrees F.

11. The method of reducing facial wrinkles as in claim 9, wherein the power source comprises rechargeable batteries.

12. The method of reducing facial wrinkles as in claim 9, wherein the spoon shaped surface comprises a heat conductive material.

13. The method of reducing facial wrinkles as in claim 9 further comprising the step of automatically activating the power source upon removing said iron from said charger.

14. The facial iron as in claim 4, wherein said switch comprises a magnetic reed switch.

15. A method of reducing facial wrinkles comprising the steps of:

connecting a spoon shaped surface to a power source and a heater;

containing said spoon shaped surface and said power source and heater in a hand-held iron;

charging said power source within said hand-held iron with a charger;

removing said iron from said charger;

activating said power source upon removal from the charger;

heating said spoon shaped surface with said power source and heater to a predetermined temperature;

maintaining said spoon shaped surface at a predetermined temperature with a control circuit;

applying said spoon shaped surface to a user's face to treat wrinkles; and returning said hand-held iron to said charger to recharge said power source.

16. The method of reducing facial wrinkles as in claim 9 further comprising the step of automatically activating the power source upon removing said iron from said charger, said step comprising using a magnetic reed switch.

17. The method of reducing facial wrinkles as in claim 15 further comprising the step of activating the power source upon removing said hand-held iron from said charger, said step comprising using a magnetic reed switch.

18. The facial iron as in claim 1 further comprising:

a three position switch, wherein a first position of said switch causes said heater to turn on upon removal from said charger;

a second position of said switch turns said heater on by hand; and a third position turns said heater off when said facial iron is not in said charger.

19. The facial iron as in claim 18, wherein said spoon shaped surface further comprises a convex surface as presented to a user.

20. The facial iron as in claim 18, wherein said first position causes said rechargeable batteries to charge when said facial iron is placed in said charger.

* * * * *